US010362863B2

(12) United States Patent
Groenke

(10) Patent No.: US 10,362,863 B2
(45) Date of Patent: Jul. 30, 2019

(54) STOWABLE SENSORY LEARNING ASSEMBLY

(71) Applicant: Roland Gregory Groenke, Oklahoma City, OK (US)

(72) Inventor: Roland Gregory Groenke, Oklahoma City, OK (US)

( * ) Notice: Subject to any disclaimer, the term of this patent is extended or adjusted under 35 U.S.C. 154(b) by 851 days.

(21) Appl. No.: 14/574,516

(22) Filed: Dec. 18, 2014

(65) Prior Publication Data

US 2016/0174703 A1 Jun. 23, 2016

(51) Int. Cl.

*A47B 19/00* (2006.01)
*A47B 21/04* (2006.01)
*A47B 21/02* (2006.01)
*A47B 41/02* (2006.01)
*A61H 1/00* (2006.01)
(Continued)

(52) U.S. Cl.

CPC .............. *A47B 19/00* (2013.01); *A47B 21/02* (2013.01); *A47B 21/04* (2013.01); *A47B 41/02* (2013.01); *A61H 1/00* (2013.01); *A61H 1/005* (2013.01); *A47B 39/06* (2013.01); *A47B 2200/0076* (2013.01); *A61H 23/02* (2013.01); *A61H 2201/0119* (2013.01); *A61H 2201/0161* (2013.01); *A61H 2201/0192* (2013.01); *A61H 2201/1635* (2013.01); *A61H 2201/5007* (2013.01); *A61H 2201/5043* (2013.01); *A61H 2205/10* (2013.01); *A61H 2205/106* (2013.01)

(58) Field of Classification Search

CPC ......... A47B 19/00; A47B 41/02; A47B 21/04; A47B 39/06
USPC .......................................................... 434/236
See application file for complete search history.

(56) References Cited

U.S. PATENT DOCUMENTS 898,492 A * 9/1908 Migrath .................. F04D 25/02 416/60
3,961,822 A * 6/1976 Daniel ................. A47C 16/025 108/50.14
(Continued)

FOREIGN PATENT DOCUMENTS

CN 2489391 Y * 5/2002

OTHER PUBLICATIONS

"Vecta Distraction Station Multi-Sensory Environments," RehabMart, https://web.archive.org/web/20130911230717/http://www.rehabmart.com/product/vecta-distraction-station-multisensory-environments-31906.html, Sep. 11, 2013.*
(Continued)

*Primary Examiner* — Samchuan C Yao
*Assistant Examiner* — Jennifer L Korb
(74) *Attorney, Agent, or Firm* — D. Ward Hobson

(57) ABSTRACT

A stowable sensory learning assembly configured to provide a multi-sensory stimulation work space for people with sensory disorders and various learning disabilities that can be efficiently stowed when not in use and efficiently and rapidly deployed when needed. The stowable sensory learning assembly includes a horizontal base connected to a vertical housing and a canopy housing, display housing, and desk housing. The display housing and desk housing are movable relative to the canopy housing between a stowed position where the desk housing and display housing are substantially parallel to the canopy housing, and a deployed position where the display housing and the desk housing are angled relative to one another to define a work space.

13 Claims, 7 Drawing Sheets

(51) Int. Cl.

| | |
|---|---|
| *A47B 39/06* | (2006.01) |
| *A61H 23/02* | (2006.01) |

(56) References Cited

U.S. PATENT DOCUMENTS

| | | | | |
|---|---|---|---|---|
| 5,387,178 | A | 2/1995 | Moses | |
| 6,092,867 | A | 7/2000 | Miller | |
| 6,733,296 | B2 * | 5/2004 | Tojek | G06Q 30/02 434/236 |
| 2004/0115603 | A1 * | 6/2004 | Reynolds | G09B 19/00 434/236 |
| 2005/0054492 | A1 * | 3/2005 | Neff | A63B 21/008 482/57 |
| 2007/0068515 | A1 * | 3/2007 | Churchill | A61L 9/12 128/200.23 |
| 2007/0100214 | A1 | 5/2007 | Steinert | |
| 2007/0243791 | A1 | 8/2007 | Stedman | |
| 2008/0308687 | A1 * | 12/2008 | Terry | A47B 96/00 248/122.1 |
| 2009/0206641 | A1 | 8/2009 | Brown, Jr. | |
| 2011/0251535 | A1 | 8/2011 | Bender | |
| 2012/0001527 | A1 | 1/2012 | Choppla | |
| 2013/0261378 | A1 | 8/2013 | Habiche | |
| 2014/0206929 | A1 * | 7/2014 | Anderson | A61M 21/00 600/28 |
| 2015/0230602 | A1 * | 8/2015 | Glockl | A47B 83/001 108/25 |

OTHER PUBLICATIONS

"The Somatron Vibroacoustic i-Sesonry Pod is the Place to Be," RehabMart, http://library.rehabmart.com/post/the-somatron-vibroacoustic-isensory-pod-it-the-place-to-be, Jul. 15, 2011.*

"Thinking Outside the Cubicle: Technology, Productivity Poised to Make the Office Desk and Chair a Thing of the Past," Huppke, Chicago Tribune, https://web.archive.org/web/20130709182642/http://articles.chicagotribune.com/2012-10-30/business/ct-biz-1029-work-advice-huppke-20121029_1_desks-cubicle-office, Oct. 30, 2012.*

"20 Visual Timers for Children with Special Needs," Rabbi Tzvi, https://www.friendshipcircle.org/blog/2012/11/06/20-visual-timers-for-children-with-special-needs/, Nov. 9, 2012 (Year: 2012).*

"Gordon Systems and GSI Publications," Gordon Systems, https://web.archive.org/web/20061113004943/http://www.gsi-add.com/attentiontraining.htm, Nov. 13, 2006 (Year: 2006).*

Somatron, i-Sensory Pod, Product Description, www.somatron.com/i-sensory.html, Aug. 21, 2014.

* cited by examiner

STOWABLE SENSORY LEARNING ASSEMBLY

BACKGROUND

People with sensory disorders and various learning disabilities, including but not limited to, Autism and Attention Deficit Hyper Activity Disorder ("ADHD"), may become easily distracted, unable to focus, and hyper-sensitive to sensory input. Sensory disorders can affect people in a variety of ways, including increased sensitivity to touch, sight, movement, sound, or smell. For example, a person with a sensory disorder may over-respond to the sensation of physical contact, light, or sound or find other sensory input uncomfortable. Alternatively, a person with a sensory disorder may under respond to sensory input or have no response at all, even to extreme sensory input, such as very hot or cold temperatures, loud sounds, or bright lights. People with sensory disorders may also have difficulty processing messages, or may have impaired muscles, joints, or motor skills. As a result, people with sensory disorders may have difficulty completing classroom activities and other learning and educational based tasks.

For example, people with sensory disorders may have difficulty sitting and focusing for extended periods of time in a traditional classroom learning environment. In a traditional learning environment, people may be over exposed to a variety of sensory input, such as light, sound, smell, or touch. Further, traditional learning environments may under expose people to a particular type of sensory input, such as sound or light, which may be beneficial to the learning process if increased and controlled.

Because people with sensory and learning disabilities may require multiple forms of sensory stimulation to maintain focus, traditional learning environments, often inhibit rather than promote learning. Educators may introduce individual tools, such as radios, exercise equipment, or textured fabric, to aid in the educational process. Unfortunately, such tools are not integrated into an efficient and convenient system. Because such traditional tools are not interconnected, it is not practical or efficient for an educator to implement multiple sensory tools simultaneously or at specific timed intervals.

For example, people with sensory disorders may have mobility difficulties or require physical stimulation simultaneously with auditory and or visual stimulation in order to effectively learn. As such, individual tools that are not interconnected are not always practical, and their usefulness decreases if they are not used simultaneously or in association with other forms of sensory stimulation. Further, because people with sensory disorders are often educated in traditional learning environments with multiple students and few educators, providing customized sensory input simultaneously to multiple students is not practical or efficient.

To that end, it would be advantageous to provide a stowable sensory learning assembly configured to provide a multi-sensory stimulation work space that can be efficiently stowed when not in use and efficiently deployed when needed. It would also be advantageous to provide a stowable sensory learning assembly that interconnects with and controls multiple sensory input tools and devices simultaneously. It is to such stowable sensory learning assembly and to methods for using thereof that exemplary embodiments of the inventive concepts disclosed and claimed herein are directed.

BRIEF DESCRIPTION OF THE SEVERAL VIEWS OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, drawings, and appendices. In the drawings.

DETAILED DESCRIPTION OF EXEMPLARY EMBODIMENTS

Figure 1:
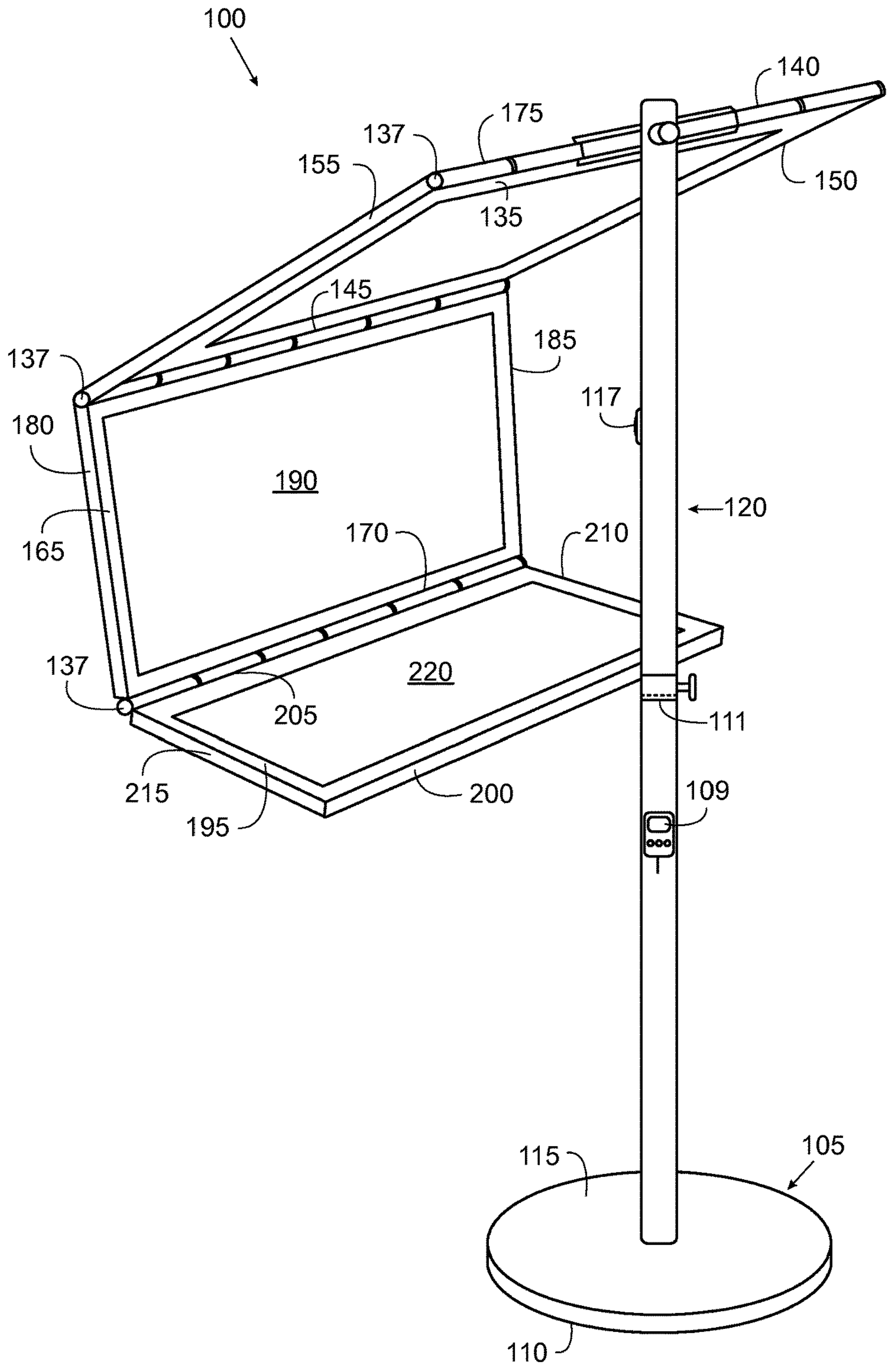
FIG. 1 is a perspective view of an exemplary embodiment of a stowable sensory learning assembly according to the inventive concepts disclosed herein shown in a deployed position.

Before explaining at least one embodiment of the inventive concepts disclosed herein in detail, it is to be understood that the inventive concepts are not limited in their application to the details of construction and the arrangements of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed.

As used herein the notation "a-n" appended to a reference numeral is intended as merely convenient shorthand to reference one, or more than one, and up to infinity, of the element or feature identified by the respective reference numeral (e.g., 100*a-n*). Similarly, a letter following a reference numeral is intended to reference an embodiment of the feature or element that may be similar, but not necessarily identical, to a previously described element or feature bearing the same reference numeral (e.g., 100, 100*a*, 100*b*, etc.). Such shorthand notations are used for purposes of clarity and convenience only, and should not be construed to limit the instant inventive concept(s) in any way, unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The inventive concepts disclosed herein are generally directed to stowable sensory learning assemblies configured to utilize multiple sensory learning tools simultaneously and to define an efficient work space for people with sensory and learning disorders. In some embodiments a stowable sensory learning assembly may include a seat and foot-rest, and in some embodiments, a stowable sensory learning assembly may include an arm member and a horizontal dispenser housing. Stowable sensory learning assemblies according to the inventive concepts disclosed herein are configured to provide sensory stimulation to users with sensory and other learning based disabilities.

Referring now to FIGS. 1-4, shown therein are exemplary embodiments of a stowable sensory learning assembly (100) constructed according to the inventive concepts disclosed herein. The stowable sensory learning assembly (100) includes a horizontal base (105) having a bottom surface (110) and a top surface (115). A vertical housing (120) having a bottom end (125) and a top end (130). The bottom end (125) connected to the top surface (115) of the horizontal base (105). A canopy housing (135) having a top end (140), a bottom end (145), and first and second sides (150 and 155) extending between the top end (140) and the bottom end (145), defining a plane (136). The top end (140) of the canopy housing (135) pivotably coupled to the vertical housing (120) at a first distance above the horizontal base (105). A display housing (165) having a bottom end (170), a top end (175), and first and second sides (180 and 185) extending between the top end (175) and the bottom end (170) defining a display screen (190). The top end (175) of the display housing (165) pivotably coupled to the bottom end (145) of the canopy housing (135). A desk housing (195) having a bottom end (200), a top end (205), and first and second sides (210 and 215) extending between the top end (205) and the bottom end (200) defining a writing surface (220). The top end (205) of the desk housing (195) pivotably coupled to the bottom end (170) of the display housing (165). The display housing (165) and the desk housing (195) are movable relative to the canopy housing (135) between a stowed position (225) where the desk housing (195) and display housing (165) are substantially parallel to the canopy housing (135), and a deployed position (230) where the display housing (165) and the desk housing (195) are angled relative to one another to define a work space.

The horizontal base (105) includes a bottom surface (110) and a top surface (115). The horizontal base (105) may be implemented as a generally planar body of any shape or size sufficient to support the stowable sensory learning assembly (100). The horizontal base (105) may be constructed of any desired material, including but not limited to, plastic, wood, metals, alloys, non-metals, steel, titanium, carbon fiber, polymers, resins, ceramics, composite materials, or combinations thereof. In some embodiments, the horizontal base (105) may be generally circular in shape, while in some embodiments the horizontal base (105) may be substantially rectangular or square. The horizontal base (105) may have any desired shape, as will be appreciated by persons of ordinary skill in the art having the benefit of the instant disclosure. Further, embodiments of the horizontal base (105) may include reinforcing or bracing structures, such as struts, ribs, braces, rods, or any other suitable reinforcing structure, or combinations thereof.

The horizontal base (105) may also be secured to a man-made structure, natural body, or object to further stabilize the stowable sensory learning assembly (100). As will be appreciated by one of ordinary skill in the art having the benefit of the instant disclosure, the man-made structure, natural body, or object may be any type of man-made structure, natural body or object, including but not limited to a floor, patio, foundation, concrete slab, rock, dirt, wood, or platform. The horizontal base (105) may be secured to the man made structure, natural body or object via fasteners, anchors, rope, footing, bolts, or any other fasteners or connectors known in the art.

The vertical housing (120) includes a bottom end (125) and a top end (130). The bottom end (125) of the vertical housing (120) connected to the top surface (115) of the horizontal base (105). The vertical housing (120) may be substantially straight or may be curved or angled. The vertical housing (120) may be constructed of any type of material capable of storing electrical and power supply components necessary for the operation of the sensory learning assembly (100). For example, the vertical housing (120) may contain electrical outlets, electrical wires, video or audio components, conduit, computers, batteries, Universal Serial Bus ("USB") ports, fans, audio speakers, fasteners, and a variety of other electronic media applications. Further, the vertical housing (120) may contain components sufficient to establish an internet or network connection with various electronic media devices and applications. The vertical housing (120) may be constructed of plastic, wood, metals, alloys, non metals, steel, titanium, carbon fiber, polymers, resins, ceramics, composite materials, or combinations thereof. In some embodiments, the vertical housing (120) may be generally circular in shape, while in some embodiments the vertical housing (120) may be substantially rectangular or square. The vertical housing (120) may have any desired shape, as will be appreciated by persons of ordinary skill in the art having the benefit of the instant disclosure. Further, embodiments of the vertical housing (120) may include reinforcing or bracing structures, such as struts, ribs, braces, rods, or any other suitable reinforcing structure, or combinations thereof. Further, embodiments of the vertical housing (120) may include a re-moveable outer sleeve or cover configured to hide at least some of the electrical components for the operation of the stowable sensory learning assembly (100). The sleeve or cover may also provide protection to a user from such electrical components and allow for convenient storage of the stowable sensory learning assembly (100) when not in use.

The bottom end (125) of the vertical housing (120) is connected to the horizontal base (105) via a threaded portion (122) that screws into an opening in the top surface (115) of the horizontal base (105) to connect and disconnect the vertical housing (120) to the horizontal base (105). It is to be appreciated that the vertical housing (120) may be connected and disconnected to the horizontal base (105) in any desired manner such as via joints, screws, bolts, adhesives, grooves, or combinations thereof.

The canopy housing (135) of the stowable sensory assembly (100) includes a bottom end (145), a top end (140), and first and second sides (150 and 155) extending between the top end (140) and the bottom end (145) defining a plane (136). As will be appreciated by one of ordinary skill in the art having the benefit of the instant disclosure, the plane (136) may be constructed from any type of material capable of providing overhead cover to a user of the stowable sensory assembly (100). For example, the plane (136) may be formed from plastic wood, metal, polymers, or the like. Further, the plane (136) may be transparent, clear, or opaque. The canopy housing (135) may be constructed from any type of material sufficient to store electrical components sufficient for the operation of the sensory learning assembly (100). For example, the canopy housing (135) may be constructed of plastic, wood, metals, alloys, non-metals, steel, titanium, carbon fiber, polymers, resins, ceramics, composite materials, or combinations thereof.

In some embodiments, the canopy housing (135) may be generally rectangular in shape, while in some embodiments the canopy housing (135) may be substantially square or circular. The canopy housing (135) may have any desired shape, as will be appreciated by persons of ordinary skill in the art having the benefit of the instant disclosure. Further, embodiments of the canopy housing (135) may include reinforcing or bracing structures, such as struts, ribs, braces, rods, or any other suitable reinforcing structure, or combinations thereof.

The top end (140) of the canopy housing (135) is pivotably coupled to the vertical housing (120) at a first distance above the horizontal base (105). The canopy housing (135) is pivotably, movably, or rotatably coupled with the vertical housing (120) such that the canopy housing (135) is movable relative to the vertical housing (120), the display housing (165) and the desk housing (195) to define a work space. The first distance is shown substantially at or near the top end (130) of the vertical housing (120). As will be appreciated by one of ordinary skill in the art having the benefit of instant disclosure, the first distance may be any desired distance above the horizontal base (105) sufficient to provide cover to a user of the stowable sensory assembly (100). For example, depending upon the height of a user of the stowable sensory assembly (100) and whether a user is sitting or standing, the first distance may be adjusted to be closer to or further away from the horizontal base (105).

In some embodiments, the top end (140) of the canopy housing (135) is pivotably coupled to the vertical housing (120) via a hinge (137), which may be implemented as a single hinge (137) substantially spanning the first and second sides (150 and 155) of the canopy housing (135), or as one or more separate hinge (137) operably coupled to the vertical housing (120). In some embodiments, the hinge (137) may also include a clamp or other mechanism operably coupled therewith so as to secure the canopy housing (135) at any desired position. In some embodiments the hinge (137) may also include one or more pneumatic, hydraulic, elastomeric, mechanical, or any other desired clamping, pivoting, or securing mechanisms so as to allow a user to safely and effortlessly deploy and stow the stowable sensory assembly (100).

Further, in some embodiments, the hinge (137) may be implemented as a locking hinge (137) configured to lock the canopy housing (135) to the vertical housing (120) relative to one another at any desired angle, or may be configured to the movement of the canopy housing (135) relative to the vertical housing (120) at any desired angle, as will be appreciated by persons of ordinary skill in the art having the benefit of the instant disclosure.

The display housing (165) of the stowable sensory assembly (100) includes a bottom end (170), a top end (175), and first and second sides (180 and 185) extending between the top end (175) and the bottom end (170) defining a display screen (190). As will be appreciated by one of ordinary skill in the art having the benefit of the instant disclosure, the display screen (190) may be any type of screen capable of displaying images or video. For example, the display screen (190) may be a television screen, computer screen, monitor, flat screen, curved screen, liquid crystal display (LCD), plasma screen, projection screen, or the like. The display housing (165) may be constructed of any type of material sufficient to store electrical and power supply components for video and image display and for the operation of the sensory learning assembly (100). The display housing (165) may be constructed of any desired material, including but not limited to, plastic, wood, metals, alloys, non-metals, steel, titanium, carbon fiber, polymers, resins, ceramics, composite materials, or combinations thereof.

In some embodiments, the display housing (165) may be generally rectangular in shape, while in some embodiments the display housing (165) may be substantially square or circular. The display housing (165) may have any desired shape, as will be appreciated by persons of ordinary skill in the art having the benefit of the instant disclosure. Further, embodiments of the display housing (165) may include reinforcing or bracing structures, such as struts, ribs, braces, rods, or any other suitable reinforcing structure, or combinations thereof.

The top end (175) of the display housing (165) is pivotably coupled to the bottom end (145) of the canopy housing (135). The display housing (165) is pivotably, movably, or rotatably coupled with the canopy housing (135) and is movable relative to the canopy housing (135) to define a work space. In some embodiments, the top end (175) of the display housing (165) is pivotably coupled to the bottom end (145) of the canopy housing (135) via a hinge (137), which may be implemented as a single hinge (137) substantially spanning the first and second sides (180 and 185) of the display housing (165), or as one or more separate hinge (137) operably coupled to the canopy housing (135). In some embodiments, the hinge (137) may include a spring or other biasing or damping mechanism operably coupled therewith, while in some embodiments the hinge (137) may include one or more pneumatic, hydraulic, elastomeric, mechanical, or any other desired biasing or damping mechanism so as to allow a user to safely and effortlessly deploy and stow the stowable sensory assembly (100), as will be appreciated by persons of ordinary skill in the art having the benefit of the instant disclosure.

Further, in some embodiments, the hinge (137) may be implemented as a locking hinge (137) configured to lock the display housing (165) to the canopy housing (135) relative to one another at any desired angle, or may be configured to limit the movement of the display housing (165) relative to the canopy housing (135) at any desired angle, as will be appreciated by persons of ordinary skill in the art having the benefit of the instant disclosure.

The desk housing (195) of the stowable sensory assembly (100) includes a bottom end (200), a top end (205), and first and second sides (210 and 215) extending between the top end (205) and the bottom end (200) defining a writing surface (220). As will be appreciated by one of ordinary skill in the art having the benefit of the instant disclosure, the writing surface (220) may be any type of surface sufficient for writing or typing, including but not limited to plastic, wood, or metal. Further, in some embodiments, the writing surface (220) may be capable of being written on. For example, the writing surface (220) may be a white-board, chalk-board, dry-erase board, or similar surface. The desk housing (195) may be constructed of any desired material, including but not limited to, plastic, wood, metals, alloys, non-metals, steel, titanium, carbon fiber, polymers, resins, ceramics, composite materials, or combinations thereof. In some embodiments, the desk housing (195) may be generally rectangular in shape, while in some embodiments the desk housing (195) may be substantially square or circular. The desk housing (195) may have any desired shape, as will be appreciated by persons of ordinary skill in the art having the benefit of the instant disclosure. Further, embodiments of the desk housing (195) may include reinforcing or bracing structures, such as struts, ribs, braces rods, or any other suitable reinforcing structure, or combinations thereof.

The top end (205) of the desk housing (195) is pivotably coupled to the bottom end (170) of the display housing (165). The desk housing (195) is pivotably, movably, or rotatably coupled with the display housing (165) and is movable relative to the display housing (165) to define a work space. In some embodiments, the top end (205) of the desk housing (195) is pivotably coupled to the bottom end (170) of the display housing (165) via a hinge (137) which may be implemented as a single hinge (137) substantially spanning the first and second sides (210 and 215) of the desk housing (195), or as one or more separate hinge (137) operably coupled to the desk housing (195). In some embodiments, the hinge (137) may include a spring or other biasing or damping mechanism operably coupled therewith, while in some embodiments the hinge (137) may include one or more pneumatic, hydraulic, elastomeric, mechanical, or any other desired biasing or damping mechanism so as to allow a user to safely and effortlessly deploy and stow the stowable sensory assembly (100), as will be appreciated by persons of ordinary skill in the art having the benefit of the instant disclosure.

Further, in some embodiments, the hinge (137) may be implemented as a locking hinge (137) configured to lock the desk housing (195) to the display housing (165) relative to one another at any desired angle, or may be configured to limit the movement of the desk housing (195) relative to the display housing (165) at any desired angle, as will be appreciated by persons of ordinary skill in the art having the benefit of the instant disclosure.

Figure 2:
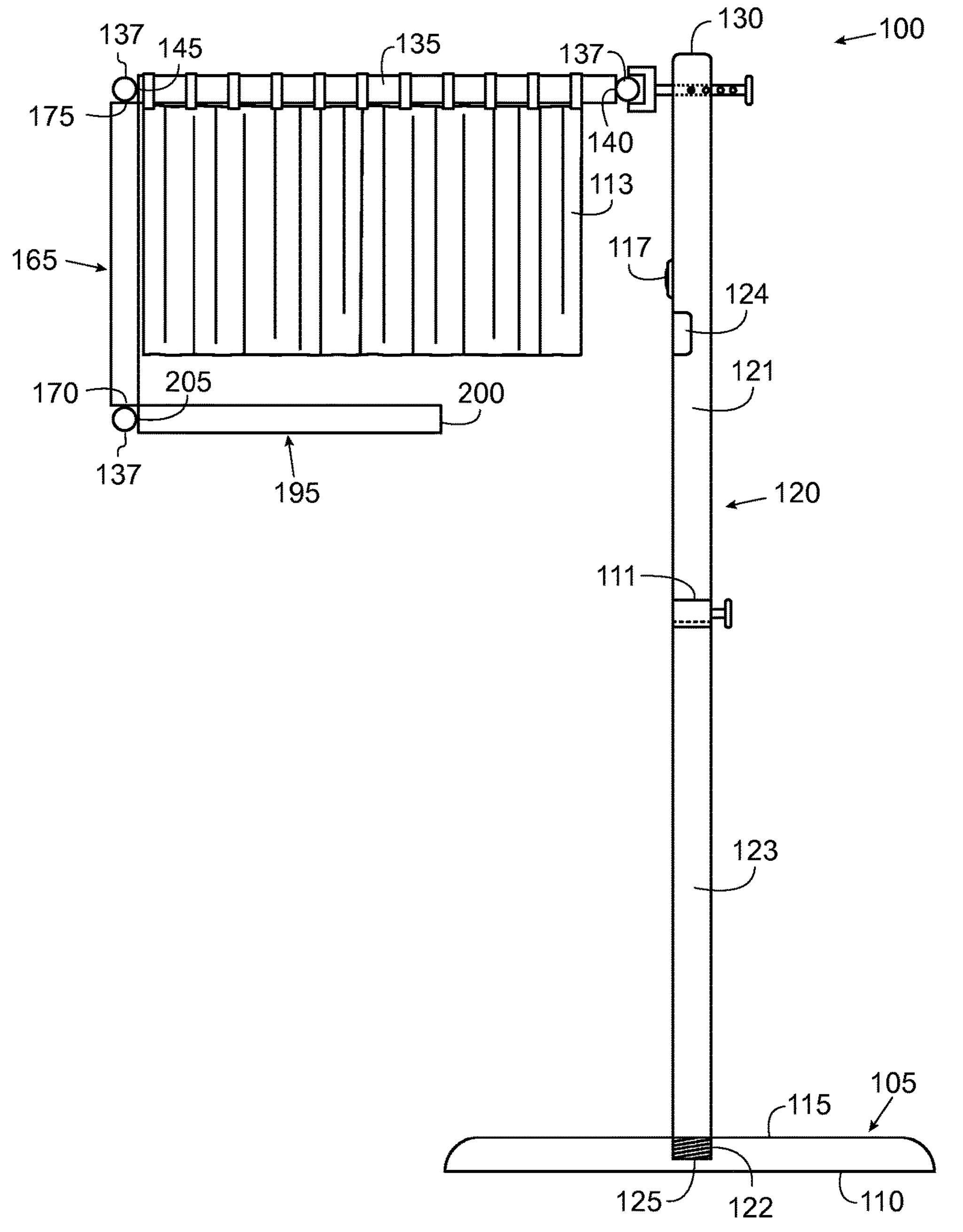
FIG. 2 is a side view of an embodiment of a stowable sensory learning assembly according to the inventive concepts disclosed herein shown in a deployed position.
Figure 3:
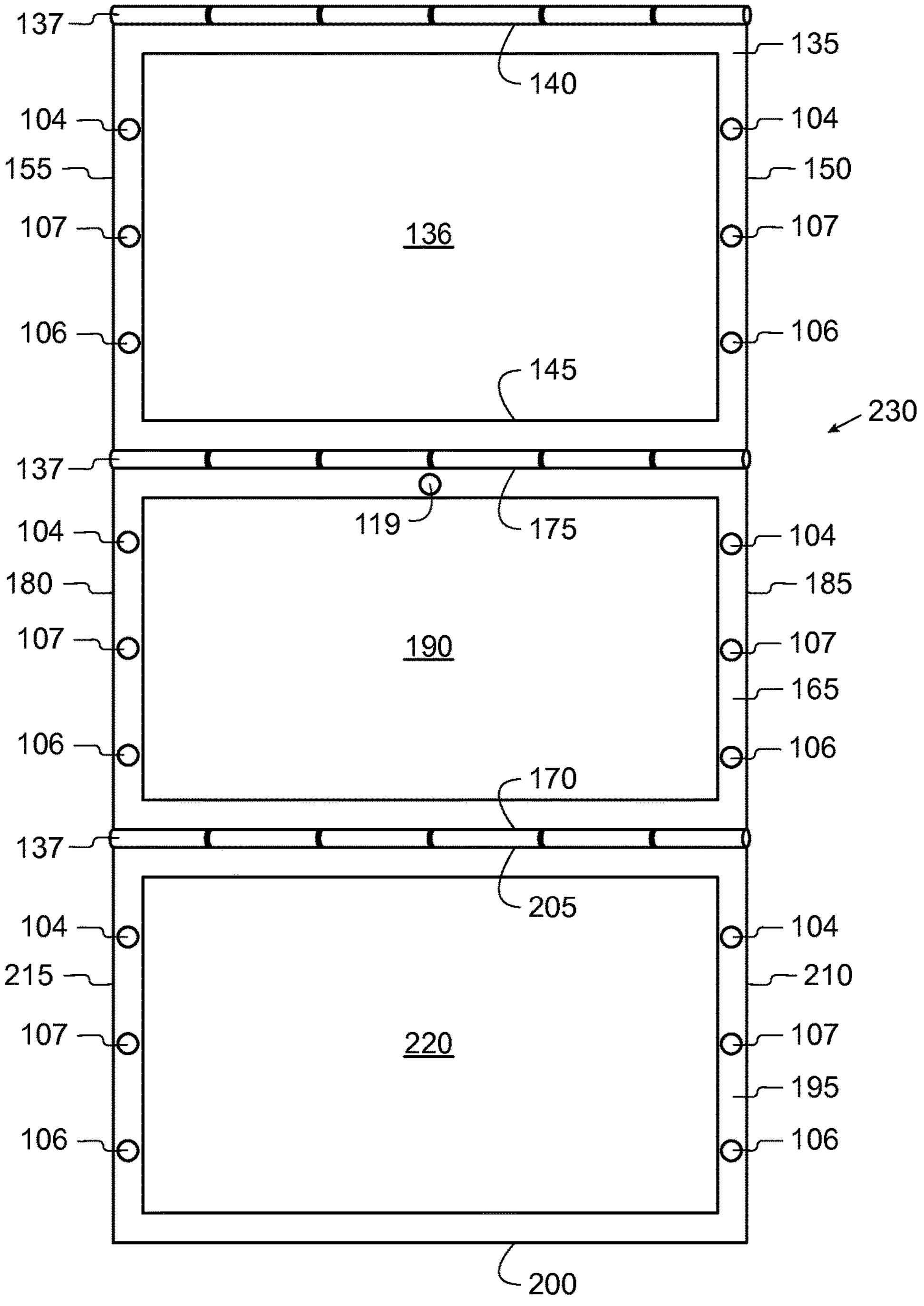
FIG. 3 is front view of an embodiment of a display housing, canopy housing, and desk housing of a stowable sensory learning assembly in a deployed position according to the present disclosure.
Figure 4:
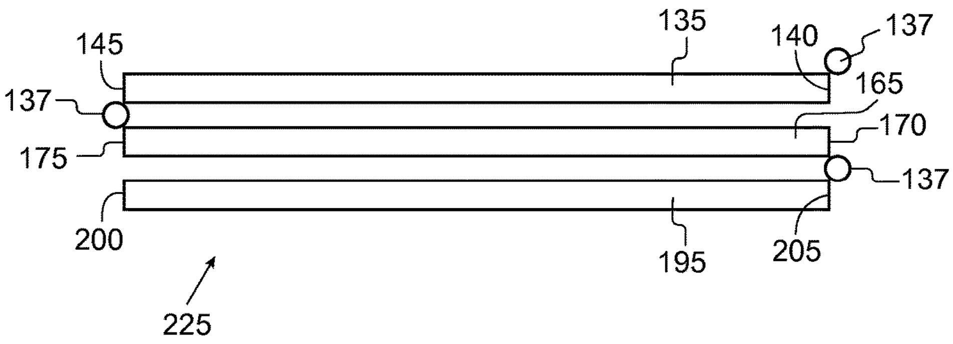
FIG. 4 is a side view of an embodiment of a display housing, canopy housing, and desk housing of a stowable sensory learning assembly in a stowed position according to the present disclosure.

The display housing (165), desk housing (195), and canopy housing (135), are movable relative to one another between a stowed position (225) where the desk housing (195) and display housing (165) are substantially parallel to the canopy housing (135), and a deployed position (230) where the display housing (165) and the desk housing (195) are angled relative to one another to define a work space. FIGS. 1-3, show the display housing (165), desk housing (195), and canopy housing 135) in the deployed position (230). FIG. 4 shows the display housing (165), desk housing (195), and canopy housing (135) in the stowed position (225).

As will be appreciated by persons of ordinary skill in the art having the benefit of the instant disclosure, when the stowable sensory learning assembly (100) is in the deployed position (230), the display housing (165) desk housing (195), and canopy housing (135), may be angled relative to one another at any desired angle sufficient to define a work space for a user. When in the deployed position (230) a user may utilize the writing surface (220) of the desk housing (195) for sensory based educational and learning tasks, including but not limited to, art, writing, typing, manipulatives, and other tasks. Further, a user may view video, images, or other media on the display screen (190) of the display housing (165) for any desired type of sensory based educational and learning tasks. When in the stowed position (225), the display housing (165), desk housing (195), and canopy housing (135), are substantially parallel to one another so that the stowable sensory learning assembly (100) may be efficiently and conveniently stowed when not in use.

As shown in FIG. 3, in some embodiments, the stowable sensory learning assembly (100) may include a means for providing light (104). As will be appreciated by one of ordinary skill in the art with the benefit of the instant disclosure, the means for providing light (104) may be light bulbs, light emitting diode "LED" lights, or any other form of light emitting source known in the art. Further, the means for providing light (104) may include fiber optic lighted tracks with alternating, chasing, or constant colored lighting. The means for providing light (104) may be connected to a power source, such as an electrical outlet or battery housed within the sensory learning assembly (100) or located external to the sensory learning assembly (100). The means for providing light (104) may emit light of various colors and frequencies and may be controlled by one or more on and off switches and one or more computers so as to provide sensory stimulation to a user at a desired time or frequency.

For example, the means for providing light (104) may emit red, yellow, and green light to provide an indication to a user of a particular task to be completed. A green light for example, may indicate that a task or the time selected for task is starting or ongoing. A yellow light, for example, may indicate that a task or the time selected for completing a task is coming to an end. A red light, for example, may indicate that a task is done or that the time selected for completing the task is done. As will be appreciated by one of ordinary skill in the art having the benefit of the instant disclosure, various colors of lights and frequencies may be implemented.

As shown in FIG. 3, in some embodiments, the stowable sensory learning assembly (100) may be configured to include a means for providing air flow (106). As will be appreciated by one of ordinary skill in the art with the benefit of the instant disclosure, the means for providing air flow (106) may include a fan connected to a power source, such as an electrical outlet or battery. The means for providing air flow (106) may also be used to produce bubbles, when operably coupled with soap or bubble solution, to attract a user and provide touch and sight sensory experience to comfort or stimulate a user. The means for providing air flow (106) may circulate air at various speeds and or frequencies and may be controlled by on and off switches and or computers housed within or external to the sensory learning assembly (100). The means for providing air flow (106) is configured to comfort and cool a user and provide movement and sensory stimulation to a user.

As shown in FIG. 3, in some embodiments, the stowable sensory learning assembly (100) may include a means for providing aroma (107). As will be appreciated by one of ordinary skill in the art, having the benefit of the instant disclosure, the means for providing aroma (107) may be a scent emitting source capable of emitting any desired scent or odor. The means for providing scent (107) may be operably coupled with a fan connected to a power source, such as an electrical outlet or battery, so as to circulate the desired aroma and provide sensory stimulation to a user. The means for providing aroma (107) may emit aroma at various speeds, frequencies or strengths so as to provide a user with sensory stimulation at desired times or intervals. The means for providing aroma (107) may also be controlled by one or more switches or computers located within the stowable sensory stimulation assembly (100) or located external to the stowable sensory stimulation assembly (100).

As shown in FIG. 1, in some embodiments, the stowable sensory learning assembly (100) may also include a means for controlling sensory stimulation (109). As will be appreciated by one of ordinary skill in the art having the benefit of the instant disclosure, the means for controlling sensory stimulation (109) may be one or more computers, a switch, or any other means known in the art for controlling electronic components. The means for controlling sensory stimulation (109) may also be connected to the internet or a computer network such that the means for controlling sensory stimulation (109) can be interfaced with and operated remotely from a computer or computers via the internet or other wireless network. Further, a user may interface with the means for controlling sensory stimulation (109) via the display screen (190), which may be a touch controlled screen, or via a computer or other electronic control device known the art. For example, a remote control, or a computer located remote from the sensory learning assembly (100).

In some embodiments, the display screen (190) may be configured to display a visual timer configured to set limits or monitor progress on a particular task or activity. For example, the visual timer may display numbers that count down or count up to indicate the end or beginning of a particular task. The visual timer may be operably coupled with the means for providing light (104) so that the frequency and color of the light may provide an indication of the time identified on the visual timer. For example, the means for providing light (104) may flash green as an activity begins, yellow as an activity comes near a deadline, and red to signify the activity is at an end. The visual timer may operate as a conditioning tool designed to train a user of the stowable sensory learning assembly (100) to meet expectations and understand visual cues as predictors to ease learning anxiety.

As shown in FIG. 2, in some embodiments, the vertical housing (120) of the stowable sensory learning assembly (100) may be telescopically extendable and retractable. In some embodiments, the vertical housing (120) may include at least two sections, a first section (121) and a second section (123). The first section (121) of the vertical housing (120) has a first outer diameter and a first inner diameter. The second section (123) of the vertical housing (120) has a second outer diameter and a second inner diameter. The second inner diameter being larger than the first outer diameter such that the first section (121) telescopically retracts into and extends out of the second section (123). The first section (121) and second section (123) of the vertical housing (105) may be connected via a fastener (111) to hold the first section (121) and second section (123) into place at a desired position. As will be appreciated by one of ordinary skill in the art the first section (121) and second section (123) may be connected via any form connector known in the art. The vertical housing (120) may be telescopically extended and retracted in any manner known in the art so as to permit the stowable sensory learning assembly (100) to be efficiently deployed when needed and stowed when not in use. Further as will be appreciated by one of ordinary skill in the art having the benefit of the instant disclosure, the vertical housing (120) may be extended or retracted to any desired length so as to be configured for users of different heights and users in standing or sitting positions.

As shown in FIG. 2, in some embodiments, the stowable sensory learning assembly (100) may include at least one curtain (113) to further define the work space. A first curtain (113) may be connected to the first side (155) of the canopy housing (135) and a second curtain (113) may be connected to the second side (150) of the canopy housing (135) to further define the work space and provide privacy and security for a user. The curtain (113) may be constructed of any desired material, including but not limited to, cloth, mesh, plastic, metal, composite materials, or combinations thereof.

The curtain (113) is configured to provide a user with an optional personal private work space to comfort the user while simultaneously providing decreased distractions to allow a user to focus in a controlled visual stimulation environment. In some embodiments, the curtain (113) may also be operably coupled with the means for providing light (104) and or the visual timer so that the curtain (113) may be implemented simultaneously with a particular task or activity or for a desired length of time. The curtain (113) may also be customized to include mascot, character, sports team logos, or any other design features.

As shown in FIG. 1, in some embodiments, the stowable sensory learning assembly (100) may include a means for projecting video (117) onto the display screen (190). The means for projecting video (117) may be located on or within the vertical housing (120) so as to project video or images onto the display screen (190). The means for projecting video (117) may be a computer, projector, camera, or other video or image capture or display means known in the art, as will be appreciated by one of ordinary skill in the art having the benefit of the instant disclosure.

As shown in FIG. 3, in some embodiments, the stowable sensory learning assembly (100) may include a means for recording video (119). The means for recording video (119) may be located within or be connected to the display housing (165). Alternatively, the means for recording video (119) may be located within or be connected to the canopy housing (135). The means for recording video (119) may be a camera, video recorder, computer, or any other recording means known in the art. The means for recording video (119) may be configured to capture discrete images or video footage for real time monitoring and to record performance assessments. The recorded video and or images may be viewed on the display screen (190) or may be viewed remotely on a computer, monitor, or other electronic media displaying device via a computer network or internet connection.

As shown in FIG. 2, in some embodiments, the stowable sensory learning assembly (100) may also include a means for providing sound (124). The means for providing sound (124) may be speakers or other sound emitting device known in the art and may include a headphone input jack. The means for providing sound (124) may be operably coupled with one or more computers via a network or internet connection. The means for providing sound (124) may be located within or on the vertical housing (120). Alternatively, the means for providing sound (124) may be located on or within the canopy housing (135), display housing (165), or desk housing (195). Sound can reinforce and embellish learning activities.

It is to be appreciated that the stowable sensory learning assembly (100) may be shipped fully or partially assembled or disassembled in the form of a kit, as will be readily appreciated by persons of ordinary skill in the art having the benefit of the instant disclosure.

A person may use the stowable sensory learning assembly (100) as follows. Under ordinary circumstances, the stowable sensory learning assembly (100) is maintained with the stowable sensory learning assembly (100) disconnected and stored for convenient use and assembly. To use the sensory learning assembly (100), a person connects the horizontal base (105) to the vertical housing (120) via the threaded portion (122). A person then connects the canopy housing (135) to the vertical housing (120). A person then configures the canopy housing (135), display housing (165) and desk housing (195) into the desired angle to define a work space. To stow or disassemble the stowable sensory learning assembly (100), a person reverses the above steps to disconnect the stowable sensory learning assembly (100) and move the canopy housing (135), display housing (165), and desk housing (195), into the stowed position (225). It is also to be appreciated that the stowable sensory learning assembly (100) may be connected to one or more stowable sensory learning assembly (100) in a circular, linear, or other configuration to provide multiple interconnected work stations. Further, it should be appreciated that the stowable sensory learning assembly (100) may be configured in various sizes, including compact sizes for use on a desk top, in association with a bed, baby stroller, or car seat.

Figure 5:
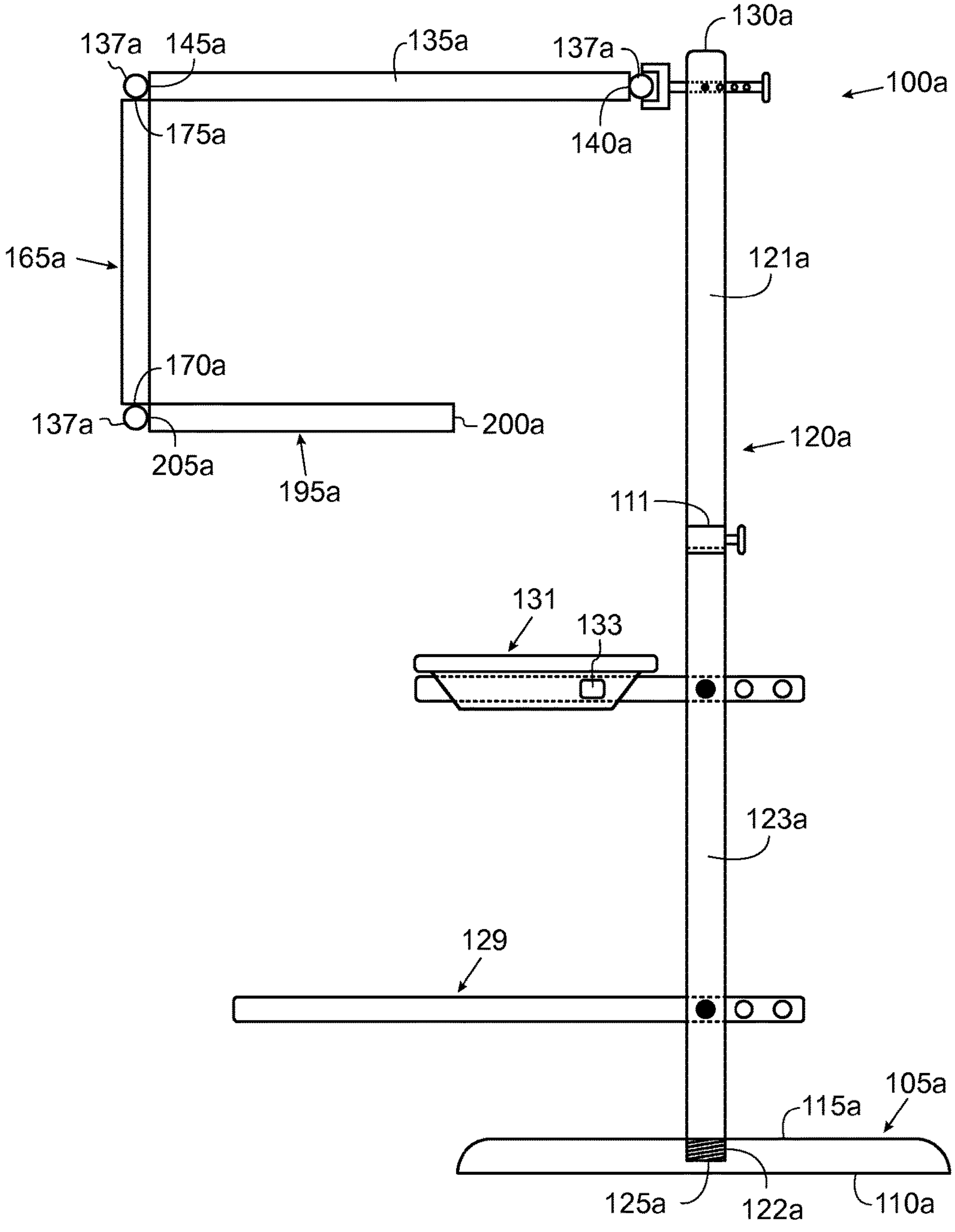
FIG. 5 is a side view of an embodiment of a stowable sensory learning assembly according to the inventive concepts disclosed herein.

Referring now to FIG. 5, shown therein is an embodiment of a stowable sensory learning assembly (100*a*) according to the inventive concepts disclosed herein. The stowable sensory learning assembly (100*a*) may be implemented similarly to the stowable sensory learning assembly (100). The stowable sensory learning assembly (100*a*) includes a horizontal base (105*a*) having a bottom surface (110*a*) and a top surface (115*a*). A vertical housing (120*a*) having a bottom end (125*a*) and a top end (130*a*), the bottom end (125*a*) of the vertical housing (120*a*) connected to the horizontal base (105*a*). A foot-rest (129) connected to the vertical housing (120*a*) at a first distance above the horizontal base (105*a*). A seat (131) connected to the vertical housing (120*a*) at a second distance above the horizontal base (105*a*). A canopy housing (135*a*) having a bottom end 145*a*), a top end (140*a*), and first and second sides extending between the top end (140*a*) and the bottom end (145*a*) defining a plane. The top end (140*a*) of the canopy housing (135*a*) pivotably coupled to the vertical housing (120*a*) at a third distance above the horizontal base (105*a*). A display housing (165*a*) having a bottom end (170*a*), a top end (175*a*), and first and second sides extending between the top end (175*a*) and the bottom end (170*a*) defining a display screen. The top end (175*a*) of the display housing (165*a*) pivotably coupled to the bottom end (145*a*) of the canopy housing (135*a*). A desk housing (195*a*) having a bottom end (200*a*), a top end (205*a*), and first and second sides extending between the top end (205*a*) and the bottom end (200*a*) defining a writing surface. The top end (205*a*) of the desk housing (195*a*) pivotably coupled to the bottom end (170*a*) of the display housing (165*a*). Wherein the display housing (165*a*) and the desk housing (195*a*) are movable relative to the canopy housing (135*a*) between a stowed position where the desk housing and display housing are substantially parallel to the canopy housing (135*a*), and a deployed position where the display housing (165*a*) and the desk housing (195*a*) are angled relative to one another to define a work space.

The foot-rest (129) may be constructed of any type of material capable of providing support for the feet of a user. The foot rest (129) is connected to the vertical housing (120*a*) at a first distance above the horizontal base (105*a*). The foot rest (129) may include raised or textured portions and padding for sensory stimulation while sitting or standing. Further, the foot-rest (129) may include a means for vibrational stimulation to provide sensory stimulation to a user. The means for providing vibrational stimulation may include a motor, or other mechanical or electronic action known in the art to provide vibration. Further, the means for providing vibrational stimulation may be operably coupled with a computer, switch or other device to control the frequency and timing of the vibration so that the vibration occurs at pre-determined time intervals.

Figure 6:
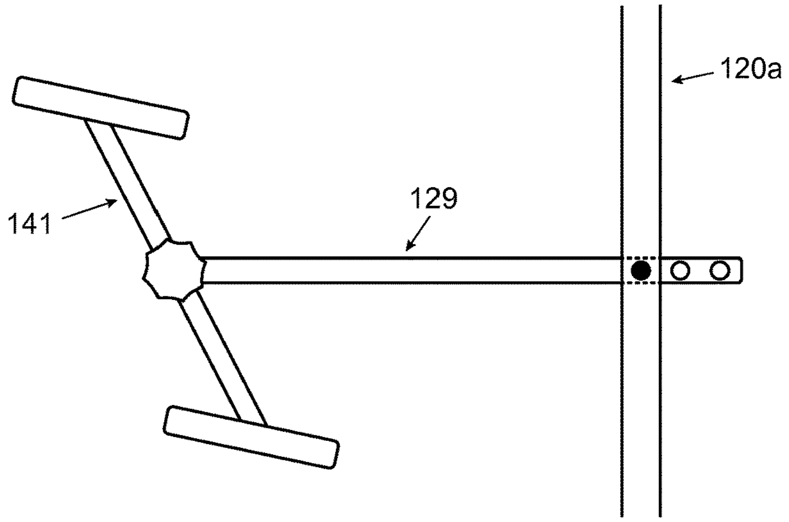
FIG. 6 is a side view of a pedal assembly of an embodiment of a stowable sensory learning assembly according to the inventive concepts disclosed herein.
Figure 7:
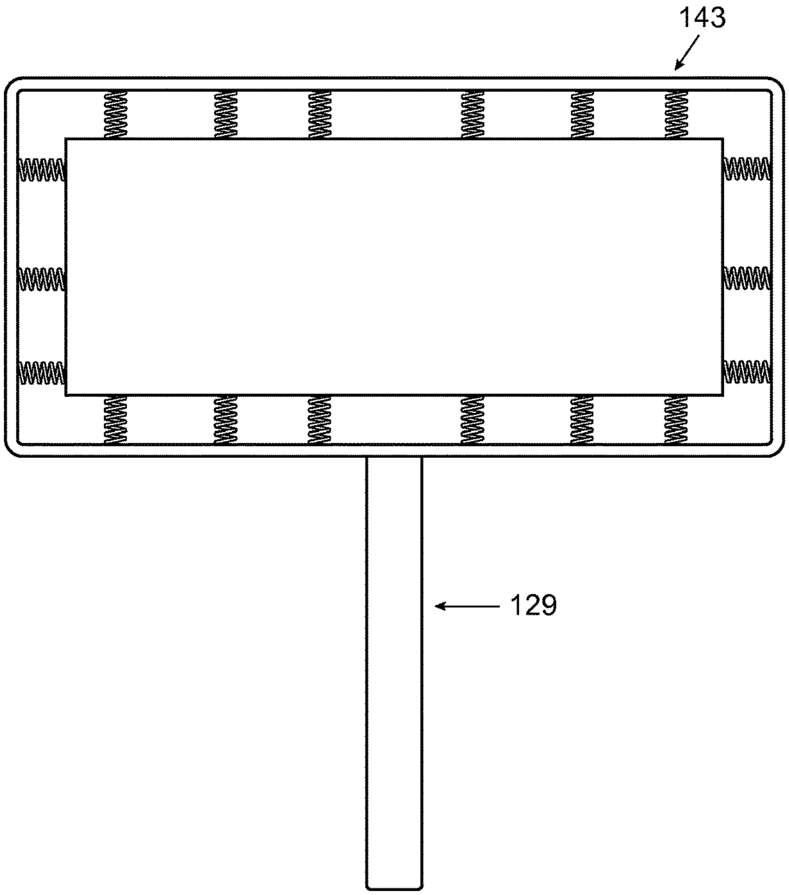
FIG. 7 is a top view of a trampoline assembly of an embodiment of a stowable sensory learning assembly according to the inventive concepts disclosed herein.

Further, as shown in FIG. 6, in some embodiments, the foot rest (129) may include a foot pedal assembly (141) for providing physical stimulation and exercise to a user. The foot pedal assembly (141) may be configured to provide a user with physical exercise, movement, stimulation, and coordination either independent of a particular task or lesson or in conjunction with a task or lesson. Learning and brain activity can be more focused when the heart rate is increased during physical activity. Further, as shown in FIG. 7, in some embodiments the foot-rest (129) may include a trampoline assembly (143) or other form of elastic surface to provide physical exercise and sensory stimulation to a user.

Referring now to FIG. 5, the seat (131) may be constructed of any type of material capable of providing support for a user. In some embodiments, the seat (131) may include a means for providing vibrational stimulation (133). The means for providing vibrational stimulation (133) may include a motor, or other mechanical or electronic action known in the art to provide vibration. Further, the means for providing vibrational stimulation may be operably coupled with a computer, switch, or other device to control the frequency and timing of the vibration so that the vibration occurs at pre-determined time intervals. The seat (131) may also include a sensory compression blanket, weighted blanket, or wrap, configured to apply pressure or sensory stimulation to a user.

Figure 8:
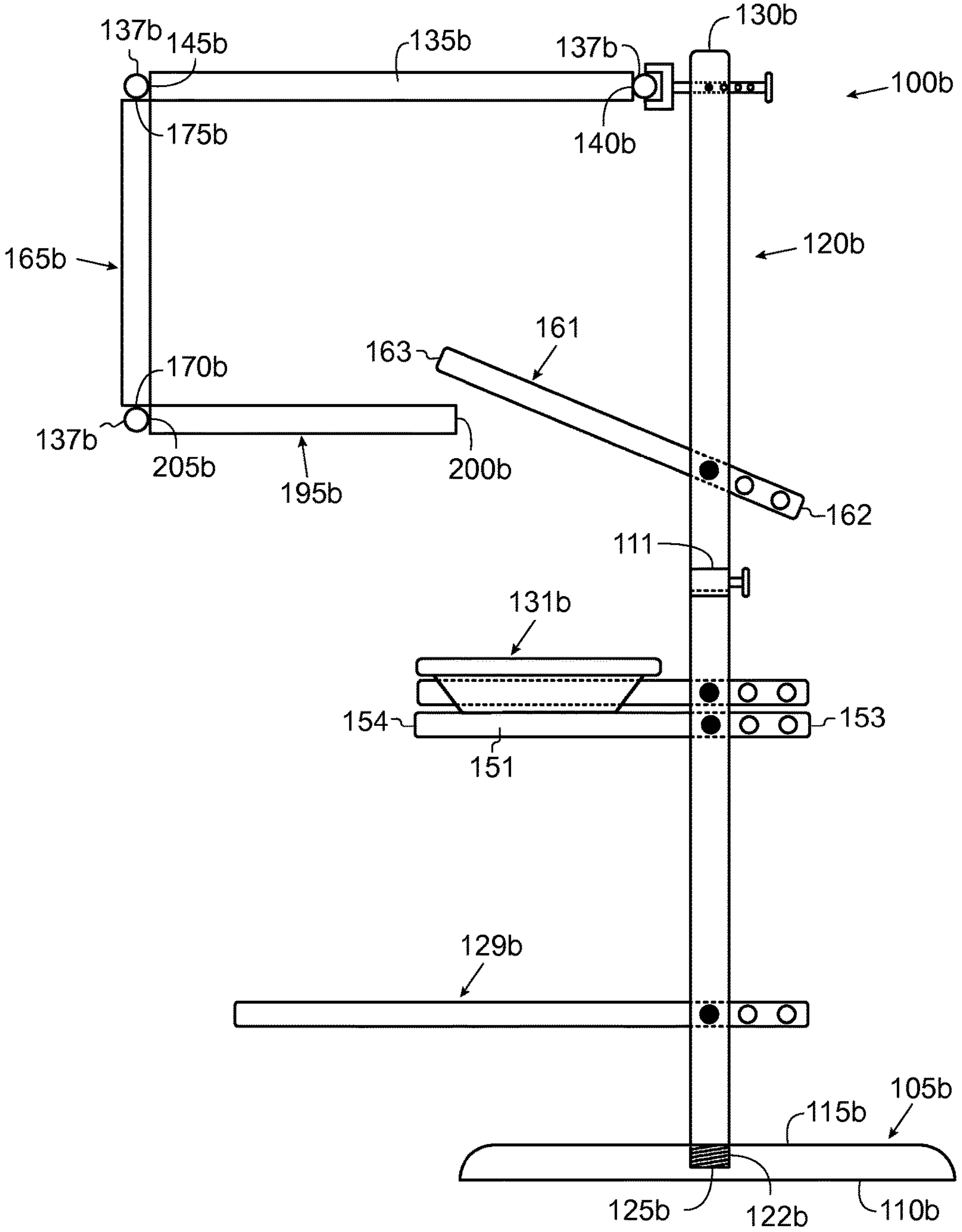
FIG. 8 is a side view of an embodiment of a stowable sensory learning assembly according to the inventive concepts disclosed herein.

Referring now to FIG. 8, shown therein is an embodiment of a stowable sensory learning assembly (100*b*) according to the inventive concepts disclosed herein. The stowable sensory learning assembly (100*b*) may be implemented similarly to the stowable sensory learning assembly (100) and (100*a*). The stowable sensory learning assembly (100*b*) includes a horizontal base (105*b*) having a bottom surface (110*b*) and a top surface (115*b*). A vertical housing (120*b*) having a bottom end (125*b*) and a top end (130*b*), the bottom end (125*b*) connected to the horizontal base (105*b*). A foot rest (129*b*) connected to the vertical housing (120*b*) at a first distance above the horizontal base (105*b*). A horizontal dispenser housing (151) having a first end (153) and a second end (154). The horizontal dispenser housing (151) connected to the vertical housing (120*b*) at a second distance above the horizontal base (105*b*). A seat (131*b*) connected to the vertical housing (120*b*) at a third distance above the horizontal base (105*b*). An arm member (161) having a first end (162) and a second end (163), the arm member (161) connected at a fourth distance above the horizontal base (105*b*).

A canopy housing (135*b*) having a bottom end (145*b*), a top end (140*b*), and first and second sides extending between the top end (140*b*) and the bottom end (145*b*) defining a plane. The top end (140*b*) of the canopy housing (135*b*) pivotably coupled to the vertical housing (120*b*) at a fifth distance above the horizontal base (105*b*). A display housing (165*b*) having a bottom end (170*b*), a top end (175*b*), and first and second sides extending between the top end (175*b*) and the bottom end (170*b*) defining a display screen. The top end (175*b*) of the display housing (165*b*) pivotably coupled to the bottom end (145*b*) of the canopy housing (135*b*). A desk housing (195*b*) having a bottom end (200*b*), a top end (205*b*), and first and second sides extending between the top end (205*b*) and the bottom end (200*b*) defining a writing surface. The top end (205*b*) of the desk housing (195*b*) pivotably coupled to the bottom end (170*b*) of the display housing (165*b*). Wherein the display housing (165*b*) and the desk housing (195*b*) are movable relative to the canopy housing (135*b*) between a stowed position where the desk housing (195*b*) and display housing (165*b*) are substantially parallel to the canopy housing (135*b*), and a deployed position where the display housing (165*b*) and the desk housing (195*b*) are angled relative to one another to define a work space.

The horizontal dispenser housing (151) may be constructed of any desired material capable of storing and dispensing rewards, including but not limited to plastic, wood, metals, alloys, non-metals, steel, titanium, carbon fiber, polymers, resins, ceramics, composite materials, or combinations thereof. The horizontal dispenser housing (151) is configured to dispense any number of desired rewards or prizes, including but not limited to, candy, toys, or other items. The horizontal dispenser housing (151) may be configured to automatically provide a visual and tangible reward for work completed upon a timed event, to reinforce a positive behavior. It should also be appreciated that the horizontal dispenser housing (151) may be manually controlled to dispense a reward upon completion of an assessed and observed task, to reinforce positive behavior.

The arm member (161) is configured to hold or support various hand-held devices, tools, or implements, including but not limited to, hand-held computers, cellular phones, computer tablets, writing implements, display screens, paper, folders, books, notebooks, and the like. It should be appreciated that the arm member (161) can be configured to support or hold any desired hand-held device, tools, or apparatus. The arm member (161) is configured to provide a stable and adjustable support that can be adjusted to accommodate a sitting or standing position and so that the hand-held device supported by the arm member (161) is within a user's field of vision.

From the above description, it is clear that the inventive concepts disclosed herein are adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the broad scope of the inventive concepts disclosed herein and defined by the appended claims.

What is claimed is:

1. A stowable sensory learning assembly, comprising:

a horizontal base having a bottom surface and a top surface;

a vertical housing having a bottom end and a top end, the bottom end connected to the top surface of the horizontal base;

a system controller positioned on the vertical housing, the system controller configured to automatically control the stowable sensory learning assembly;

a canopy housing in communication with the system controller, the canopy housing configured to provide sensory stimulation, the canopy housing having a bottom end, a top end, and first and second sides extending between the top end and the bottom end defining a plane, the top end of the canopy housing pivotably coupled to the vertical housing at a first distance above the horizontal base;

a display housing in communication with the system controller, the display housing configured to provide sensory stimulation, the display housing having a bottom end, a top end, and first and second sides extending between the top end and the bottom end defining a display screen configured to provide sensory stimulation, the top end of the display housing pivotably coupled to the bottom end of the canopy housing, wherein the display screen is configured to provide a visual indication of progress towards completion of a task, wherein a green light indicates the beginning of the task, a yellow light indicates the task is coming to an end and a red light indicates completion of the task;

a desk housing in communication with the system controller, the desk housing configured to provide sensory stimulation, the desk housing having a bottom end, a top end, and first and second sides extending between the top end and the bottom end defining a writing surface configured to provide sensory stimulation, the top end of the desk housing pivotably coupled to the bottom end of the display housing;

wherein the display housing and the desk housing are automatically movable via the system controller relative to the canopy housing between a stowed position where the desk housing and display housing are substantially parallel to the canopy housing, and a deployed position where the display housing and the desk housing are angled relative to one another to define a work space;

an automated reward dispenser in communication with the system controller, the automated reward dispenser connected to the vertical housing at a second distance above the horizontal base, wherein the automated reward dispenser is configured to automatically provides a reward concurrently with completion of the task displayed on the display screen; and a remote computer configured for remotely controlling the system controller via a wireless network.

2. The stowable sensory learning assembly of claim 1, further comprising a means for providing light.

3. The stowable sensory learning assembly of claim 1, further comprising a means for providing air flow.

4. The stowable sensory learning assembly of claim 1, further comprising a means for providing aroma.

5. The stowable sensory learning assembly of claim 1, wherein the vertical housing is telescopically extendable and retractable.

6. The stowable sensory learning assembly of claim 1, wherein the first side and the second side of the canopy housing further comprise a curtain, adapted to define the work space and provide privacy.

7. The stowable sensory learning assembly of claim 1, wherein the vertical housing further comprises a means for projecting video.

8. The stowable sensory learning assembly of claim 1, wherein the display housing further includes a means for recording video.

9. A stowable sensory learning assembly, comprising:

a horizontal base having a bottom surface and a top surface;

a vertical housing having a bottom end and a top end, the bottom end connected to the top surface of the horizontal base;

a system controller positioned on the vertical housing, the system controller configured to automatically control the stowable sensory learning assembly;

a foot-rest in communication with the system controller, the foot-rest configured to provide sensory stimulation, the foot-rest connected to the vertical housing at a first distance above the horizontal base;

a seat in communication with the system controller, the seat configured to provide sensory stimulation, the seat connected to the vertical housing at a second distance above the horizontal base;

a canopy housing in communication with the system controller, the canopy housing configured to provide sensory stimulation, the canopy housing having a bottom end, a top end, and first and second sides extending between the top end and the bottom end defining a plane, the top end of the canopy housing pivotably coupled to the vertical housing at a third distance above the horizontal base;

a display housing in communication with the system controller, the display housing configured to sensory stimulation, the display housing having a bottom end, a top end, and first and second sides extending between the top end and the bottom end defining a display screen providing sensory stimulation, the top end of the display housing pivotably coupled to the bottom end of the canopy housing, wherein the display screen is configured to automatically provides a visual indication of progress towards completion of a task, wherein a green light indicates the beginning of the task, a yellow light indicates the task is coming to an end and a red light indicates completion of the task;

a desk housing in communication with the system controller, the desk housing configured to provide sensory stimulation, the desk housing having a bottom end, a top end, and first and second sides extending between the top end and the bottom end defining a writing surface configured to provide sensory stimulation, the top end of the desk housing pivotably coupled to the bottom end of the display housing;

wherein the display housing and the desk housing are automatically movable via the system controller relative to the canopy housing between a stowed position where the desk housing and display housing are substantially parallel to the canopy housing, and a deployed position where the display housing and the desk housing are angled relative to one another to define a work space;

an automated reward dispenser in communication with the system controller, the automated reward dispenser connected to the vertical housing above the horizontal base, wherein the automated reward dispenser is configured to automatically provide a reward concurrently upon completion of the task displayed on the display screen; and a remote computer configured to remotely controlling the system controller via a wireless network.

10. The stowable sensory learning assembly of claim 9, wherein the foot-rest comprises a pedal assembly for providing physical stimulation.

11. The stowable sensory learning assembly of claim 9, wherein the foot-rest comprises a trampoline assembly for providing physical stimulation.

12. The stowable sensory learning assembly of claim 9, wherein the seat comprises a means for providing vibrational stimulation.

13. A stowable sensory learning assembly, comprising:

a horizontal base having a bottom surface and a top surface;

a vertical housing having a bottom end and a top end, the bottom end connected to the top surface of the horizontal base;

a system controller positioned on the vertical housing, the system controller configured to automatically control the stowable sensory learning assembly;

a foot-rest in communication with the system controller, the foot-rest configured to provide sensory stimulation, the foot-rest connected to the vertical housing at a first distance above the horizontal base;

a seat in communication with the system controller, the seat configured to provide sensory stimulation, the seat connected to the vertical housing at a third distance above the horizontal base;

an arm member in communication with the system controller, the arm member configured to provide sensory stimulation, the arm member having a first end and a second end, the first end of the arm member connected at a fourth distance above the horizontal base;

a canopy housing in communication with the system controller, the canopy housing configured to provide sensory stimulation, the canopy housing having a bottom end, a top end, and first and second sides extending between the top end and the bottom end defining a plane, the top end of the canopy housing pivotably coupled to the vertical housing at a fifth distance above the horizontal base;

a display housing in communication with the system controller, the display housing configured to provide sensory stimulation, the display housing having a bottom end, a top end, and first and second sides extending between the top end and the bottom end defining a display screen configured to provide sensory stimulation, the top end of the display housing pivotably coupled to the bottom end of the canopy housing;

wherein the display screen is configured to automatically provides a visual indication of progress towards completion of a task, wherein a green light indicates the beginning of the task, a yellow light indicates the task is coming to an end and a red light indicates completion of the task;

a desk housing in communication with the system controller, the desk housing configured to provide sensory stimulation, the desk housing having a bottom end, a top end, and first and second sides extending between the top end and the bottom end defining a writing surface configured to provide sensory stimulation, the top end of the desk housing pivotably coupled to the bottom end of the display housing; and wherein the display housing and the desk housing are movable relative to the canopy housing between a stowed position where the desk housing and display housing are substantially parallel to the canopy housing, and a deployed position where the display housing and the desk housing are angled at a first angle relative to one another to define a work space;

an automated reward dispenser in communication with the system controller, the automated reward dispenser connected to the vertical housing at a second distance above the horizontal base, wherein the automated reward dispenser is configured to automatically provides a reward concurrently upon completion of the task displayed on the display screen; and a remote computer configured to remotely controlling the system controller via a wireless network.

* * * * *